United States Patent [19]

Marsella et al.

[11] Patent Number: 5,972,431
[45] Date of Patent: Oct. 26, 1999

[54] CYCLIC UREA SURFACTANTS

[75] Inventors: John Anthony Marsella, Allentown; Kevin Rodney Lassila, Macungie, both of Pa.

[73] Assignee: Air Products and Chemicals, Inc., Allentown, Pa.

[21] Appl. No.: 09/124,326

[22] Filed: Jul. 29, 1998

[51] Int. Cl.$^6$ ........................................................ B05D 3/02
[52] U.S. Cl. ................................................................ 427/384
[58] Field of Search ............................................... 427/384

[56] References Cited

U.S. PATENT DOCUMENTS

| | | | |
|---|---|---|---|
| 3,876,657 | 4/1975 | Aelony et al. | 260/309.7 |
| 4,677,131 | 6/1987 | Higuchi et al. | 514/392 |
| 5,098,478 | 3/1992 | Krishnan et al. | 106/23 |
| 5,562,762 | 10/1996 | Mrvos et al. | 106/22 H |

FOREIGN PATENT DOCUMENTS 4341984  6/1995  Germany .

OTHER PUBLICATIONS

Schwartz, J., "The Importance of Low Dynamic Surface Tension in Waterborne Coatings", Journal of Coatings Technology, Sep. 1992.

Wirth, W.; Storp, S.; Jacobsen, W., "Mechanisms Controlling Leaf Retention of Agricultural Spray Solutions", Pestic. Sci. 1991, 33, 411–420.

Medina, S. W.: Sutovich, M. N., "Using Surfactants to Formulate VOC Compliant Waterbased Inks", Am. Ink Maker 1994, 72, (2) 32–38.

Nomura, et al., "Preparation of Cyclic Ureas from Carbondioxide Diamines Catalyzed by Triphenylstibine Oxide" Ind. Eng. Chem. Res. 1987, 26 1056–1059.

Naumov, et al., "N–Acyl– and N–Alkyl–Substituted Ethyleneureas", Khimiya Geteotsikl. Soedin. 1973, 1, 90–93.

Langmuir 1986, 2, 428–432.

*Primary Examiner*—Erma Cameron
*Attorney, Agent, or Firm*—Michael Leach

[57] ABSTRACT

This invention provides water-based compositions, particularly coating, ink, and agricultural compositions, manifesting reduced equilibrium and dynamic surface tension by the incorporation of a surface tension reducing amount of certain cyclic urea compounds of the structure

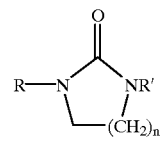

where R is a C6 to C12 alkyl group or R"O—$(CH_2)_m$-, R' is hydrogen or methyl, R" is a C4 to C12 alkyl group, m is 2–4 and n is 1 or 2.

9 Claims, No Drawings

CYCLIC UREA SURFACTANTS

FIELD OF THE INVENTION

The invention relates to the use of cyclic ureas to reduce the surface tension in water-based systems.

BACKGROUND OF THE INVENTION

The ability to reduce the surface tension of water is of great importance in waterborne coatings, inks, adhesives, and agricultural formulations because decreased surface tension translates to enhanced substrate wetting in actual formulations. Surface tension reduction in water-based systems is generally achieved through the addition of surfactants. Performance attributes resulting from the addition of surfactants include enhanced surface coverage, fewer defects, and more uniform distribution. Equilibrium surface tension performance is important when the system is at rest. However, the ability to reduce surface tension under dynamic conditions is of great importance in applications where high surface creation rates are utilized. Such applications include spraying, rolling and brushing of coatings or spraying of agricultural formulations, or high speed gravure or ink-jet printing. Dynamic surface tension is a fundamental quantity which provides a measure of the ability of a surfactant to reduce surface tension and provide wetting under such high speed application conditions.

Traditional nonionic surfactants such as alkylphenol or alcohol ethoxylates, and ethylene oxide (EO)/propylene oxide (PO) copolymers have excellent equilibrium surface tension performance but are generally characterized as having poor dynamic surface tension reduction. In contrast, certain anionic surfactants such as sodium dialkyl sulfosuccinates can provide good dynamic results, but these are very foamy and impart water sensitivity to the finished coating.

There is a need for a family of surfactants which provide good equilibrium and dynamic surface tension properties, are low-foaming and would be widely accepted in the coating, ink, adhesive, and agricultural formulation industries.

The importance of reducing equilibrium and dynamic surface tension in applications such as coatings, inks, and agricultural formulations is well-appreciated in the art.

Low dynamic surface tension is of great importance in the application of waterborne coatings. In an article, Schwartz, J. "*The Importance of Low Dynamic Surface Tension in Waterborne Coatings*", Journal of Coatings Technology, September 1992, there is a discussion of surface tension properties in waterborne coatings and a discussion of dynamic surface tension in such coatings. Equilibrium and dynamic surface tension were evaluated for several surface active agents. It is pointed out that low dynamic surface tension is an important factor in achieving superior film formation in waterborne coatings. Dynamic coating application methods require surfactants with low dynamic surface tensions in order to prevent defects such as retraction, craters, and foam.

Efficient application of agricultural products is also highly dependent on the dynamic surface tension properties of the formulation. In an article, Wirth, W.; Storp, S.; Jacobsen, W. "*Mechanisms Controlling Leaf Retention of Agricultural Spray Solutions*"; Pestic. Sci. 1991, 33, 411–420, the relationship between the dynamic surface tension of agricultural formulations and the ability of these formulations to be retained on a leaf was studied. These workers observed a good correlation between retention values and dynamic surface tension, with more effective retention of formulations exhibiting low dynamic surface tension.

Low dynamic surface tension is also important in high-speed printing as discussed in the article "*Using Surfactants to Formulate VOC Compliant Waterbased Inks*", Medina, S. W.; Sutovich, M. N. Am. Ink Maker 1994, 72 (2), 32–38. In this article, it is stated that equilibrium surface tensions (ESTs) are pertinent only to ink systems at rest. EST values, however, are not good indicators of performance in the dynamic, high speed printing environment under which the ink is used. Dynamic surface tension is a more appropriate property. This dynamic measurement is an indicator of the ability of the surfactant to migrate to a newly created ink/substrate interface to provide wetting during high speed printing.

U.S. Pat. No. 5,098,478 discloses water-based ink compositions comprising water, a pigment, a nonionic surfactant and a solubilizing agent for the nonionic surfactant. Dynamic surface tension in ink compositions for publication gravure printing must be reduced to a level of about 25 to 40 dynes/cm to assure that printability problems will not be encountered.

U.S. Pat. No. 5,562,762 discloses an aqueous jet ink of water, dissolved dyes and a tertiary amine having two polyethoxylate substituents and that low dynamic surface tension is important in ink jet printing.

Substituted cyclic ureas have been reported to have utility in many applications. Nomura et al, *Ind. Eng. Chem. Res.* 1987, 26, 1056–1059, state these materials are useful as intermediates for medicines and resins and directly as chemotherapeutic agents, delignification reagents, and in cosmetics.

Likewise, U.S. Pat. No. 3,876,657 discloses 1-alkyl-2-imidazolidones (ethylene ureas) as having recognized utility as bactericides, central nervous system depressants, plant growth promoters, female fly sterilants, adhesives, textile treating agents, and as monomers for deriving polymers and copolymers.

In addition, Naumov et al, *Khimiya Geteotsikl. Soedin.* 1973, 1, 90–93, state these materials are useful as biologically active compounds, specifically as insecticides and insect repellents. Despite this extensive listing of utility, alkylated cyclic ureas have not been reported to have utility as surface tension reducing agents in water. In fact, Kanetani et al, *Chem. Abs.* 98:145450, converted long chain N-alkylimidazolidones (C8, C10, C12, C14, C16) to the propane sultone derivatives in order to make useful surfactants.

DE 4,341,984 discloses that a very large number of ureas and cyclic ureas, including N-methyl-N'-octyl propyleneurea, act as crystallization inhibitors for azole derivative fungicides, such as triazolyl methyl compounds, in aqueous solution.

U.S. Pat. No. 4,677,131 discloses substituted cyclic ureas have efficacy for enhancing drug absorption through the skin for therapeutic or diagnostic purposes. The emphasis appears to be on utilizing the strong hydrogen bonding properties for these materials.

SUMMARY OF THE INVENTION

This invention provides water-based compositions containing an organic or inorganic compound, particularly aqueous organic coating, ink, and agricultural compositions, having reduced equilibrium and dynamic surface tension by incorporation of an effective amount of a cyclic urea compound of the following structure:

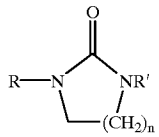

where R is a C6 to C12 alkyl group or R"O—$(CH_2)_m$-, R' is hydrogen or methyl, R" is a C4 to C12 alkyl group, m is 2–4 and n is 1 or 2, provided the organic compound is not an azole derivative fungicide. It is desirable that an aqueous solution of the cyclic urea demonstrates a dynamic surface tension of less than 45 dynes/cm at a concentration of $\leq$5 wt % in water at 23° C. and 1 bubble/second according to the maximum-bubble pressure method. The maximum-bubble-pressure method of measuring surface tension is described in *Langmuir* 1986, 2, 428–432, which is incorporated by reference.

Also provided is a method for lowering the equilibrium and dynamic surface tension of aqueous compositions by the incorporation of these cyclic urea compounds.

Also provided is a method for applying a water-based inorganic or organic compound-containing composition to a surface to partially or fully coat the surface with the water-based composition, the composition containing an effective amount of a cyclic urea compound of the above structure for reducing the dynamic surface tension of the water-based composition.

There are significant advantages associated with the use of these cyclic ureas in water-based organic coatings, inks, and agricultural compositions and these advantages include:

- an ability to formulate water-borne coatings, inks, and agricultural compositions which may be applied to a variety of substrates with excellent wetting of substrate surfaces including contaminated and low energy surfaces;
- an ability to provide a reduction in coating or printing defects such as orange peel and flow/leveling deficiencies;
- an ability to produce water-borne coatings and inks which have low volatile organic content, thus making these surfactants environmentally favorable; and
- an ability to formulate coating and ink compositions capable of high speed application.

Because of their excellent surfactant properties and the ability to control foam, these materials are likely to find use in many applications in which reduction in dynamic and equilibrium surface tension and low foam are important. Applications in which low foam is important include various wet-processing textile operations, such as dyeing of fibers, fiber souring, and kier boiling, where low-foaming properties would be particularly advantageous; they may also have applicability in soaps, water-based perfumes, shampoos, and various detergents where their marked ability to lower surface tension while simultaneously producing substantially no foam would be highly desirable.

Applications in which the high foaming character of some of the compounds of the invention would be advantageous include ore flotation and mining, carpet shampoos, shaving cream and the like.

DETAILED DESCRIPTION OF THE INVENTION

This invention relates to the use of compounds of the formula

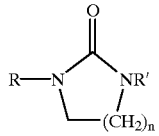

where R is a C6 to C12 alkyl group or R"O—$(CH_{2m}$-, R' is hydrogen or methyl, R" is a C4 to C12 alkyl group, m is 2–4 and n is I or 2, for the reduction of equilibrium and dynamic surface tension in water-based compositions containing an organic compound, particularly coating, ink, and agricultural compositions containing organic compounds such as polymeric resins, herbicides (excluding azole derivative fungicides), insecticides or plant growth modifying agents. It is desirable that an aqueous solution of the cyclic urea demonstrates a dynamic surface tension of less than 45 dynes/cm at a concentration of $\leq$5 wt % in water at 23° C. and 1 bubble/second according to the maximum-bubble-pressure method. The maximum-bubble-pressure method of measuring surface tension is described in *Langmuir* 1986, 2, 428–432, which is incorporated by reference.

In one aspect of the invention the N-higher alkyl and alkoxyalkyl cyclic ureas of the formula

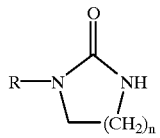

display excellent ability to reduce equilibrium and dynamic surface tension while producing substantially no foam.

Another aspect of this invention which is particularly advantageous is that the compounds of the formula

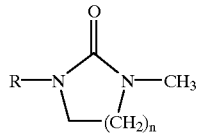

produce relatively high quantities of foam, and may therefore find application in many areas in which the formation of foam is important. Such applications may include ore flotation and mining applications, carpet shampoos, shaving cream, and the like. It was not anticipated that such a high degree of control of the foaming characteristic of these compounds could be achieved through the seemingly innocuous interchange of hydrogen and methyl.

These materials may be prepared by reacting a suitable diamine with urea:

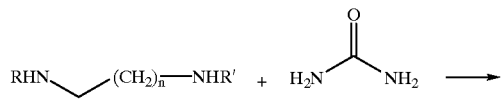

-continued

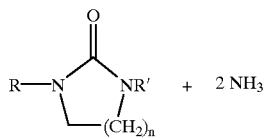

This is the preferred route for commercial production.

Alternatively, the compounds of the invention may be prepared by reaction of a suitable cyclic urea with an alkyl halide in the presence of a base and an optional solvent:

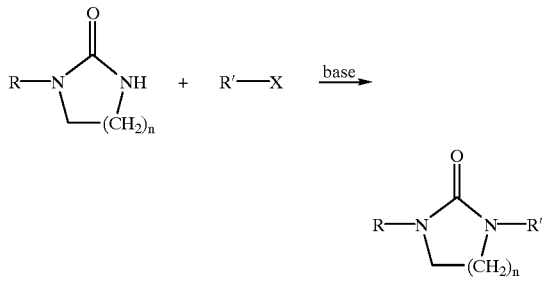

where

R is a higher alkyl group or R" and R' is methyl or

R is methyl and R' is a higher alkyl group or R" or

R is hydrogen and R' is a higher alkyl group or R".

In these descriptions, the "higher alkyl group" may be a linear, branched, or cyclic C6 to C12 hydrocarbon moiety. In general, lower numbers of alkyl carbon or a higher degree of branching will increase the solubility of the surfactant but decrease the efficiency (i.e. a greater amount will be required to obtain a given reduction in surface tension). Examples of suitable higher alkyl groups include 1-hexyl, 2-hexyl, 3-hexyl, cyclohexyl, 1-octyl, 2-ethylhexyl, 2-octyl, 3-octyl, isooctyl, cyclooctyl, n-nonyl, 2-nonyl, 3-nonyl, 4-nonyl, isononyl, n-decyl, isodecyl, 2-decyl, 3-decyl, n-dodecyl, cyclododecyl, and the like. Of course, this list is not comprehensive, and the particular alkyl group chosen for a particular use will depend on the performance characteristics required for that application. Derivatives in which the alkyl group is a mixture of isomers are also suitable for the practice of this invention. C7 to C10 hydrocarbon derivatives are preferred and C8 hydrocarbon derivatives are especially preferred.

Compounds in which the higher alkyl group contains ether linkages, i.e., R"O—(CH$_2$)$_m$-, are also suitable for use in this invention, as illustrated by the structure

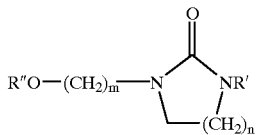

where R" is a C4 to C12 alkyl group, m is 2–4, n is 1 or 2, and R' is hydrogen or methyl. Examples of suitable C4 to C12 alkyl groups include 1-butyl, 2-butyl, t-butyl, 1-pentyl, 2-pentyl, 3-pentyl, neopentyl, 1-hexyl, 2-hexyl, 3-hexyl, cyclohexyl, 1-octyl, 2-ethylhexyl, 2-octyl, 3-octyl, isooctyl, cyclooctyl, n-nonyl, 2-nonyl, 3-nonyl, 4-nonyl, isononyl, n-decyl, isodecyl, 2-decyl, 3-decyl, n-dodecyl, cyclododecyl, and the like. Derivatives in which R" is C6 to C10 alkyl and m is 3 are preferred, although the particular choice will depend on the properties required for a specific application.

The cyclic ureas are suitable for use in an aqueous composition comprising in water an inorganic compound which is a mineral ore or a pigment or an organic compound which is a pigment, a polymerizable monomer, such as addition, condensation and vinyl monomers, an oligomeric resin, a polymeric resin, a detergent, a caustic cleaning agent, a herbicide, especially a herbicide for chlorophyll-containing plants, an insecticide, or a plant growth modifying agent.

An amount of the cyclic urea compound that is effective to reduce the equilibrium and/or dynamic surface tension of the water-based, organic compound-containing composition is added. Such effective amount may range from 0.001 to 20 g/100 mL, preferably 0.01 to 10 g/100 mL, of the aqueous composition. Naturally, the most effective amount will depend on the particular application and the solubility of the particular cyclic urea.

In the following water-based organic coating, ink, and agricultural compositions containing a cyclic urea according to the invention, the other listed components of such compositions are those materials well known to the workers in the relevant art.

A typical water-based organic coating composition to which the cyclic urea surfactants of the invention may be added would comprise the following components in an aqueous medium at 30 to 80% solids:

| Typical Water-Based Organic Coating Composition | |
|---|---|
| 0 to 50 wt % | Pigment Dispersant/Grind Resin |
| 0 to 80 wt % | Coloring Pigments/Extender Pigments/Anti-Corrosive Pigments/Other Pigment Types |
| 5 to 99.9 wt % | Water-Borne/Water-Dispersible/Water-Soluble Resins |
| 0 to 30 wt % | Slip Additives/Antimicrobials/Processing Aids/Defoamers |
| 0 to 50 wt % | Coalescing or Other Solvents |
| 0.01 to 10 wt % | Surfactant/Wetting Agent/Flow and Leveling Agents |
| 0.01 to 5 wt % | Cyclic Urea |

A typical water-based ink composition to which the cyclic urea surfactants of the invention may be added would comprise the following components in an aqueous medium at 20 to 60% solids:

| Typical Water-Based Ink Composition | |
|---|---|
| 1 to 50 wt % | Pigment |
| 0 to 50 wt % | Pigment Dispersant/Grind Resin |
| 0 to 50 wt % | Clay base in appropriate resin solution vehicle |
| 5 to 99.9 wt % | Water-Borne/Water-Dispersible/Water-Soluble Resins |
| 0 to 30 wt % | Coalescing Solvents |
| 0.01 to 10 wt % | Surfactant/Wetting Agent |
| 0.01 to 10 wt % | Processing Aids/Defoamers/Solubilizing Agents |
| 0.01 to 5 wt % | Cyclic Urea |

A typical water-based agricultural composition to which the cyclic urea surfactants of the invention may be added would comprise the following components in an aqueous medium at 0.1 to 80% ingredients:

| Typical Water-Based Agricultural Composition | |
| --- | --- |
| 0.1 to 50 wt % | Insecticide or Plant Growth Modifying Agent |
| 0.01 to 10 wt % | Surfactant |
| 0 to 5 wt % | Dyes |
| 0 to 20 wt % | Thickeners/Stabilizers/Co-surfactants/Gel Inhibitors/Defoamers |
| 0 to 25 wt % | Antifreeze |
| 0.1 to 50 wt % | Cyclic Urea |

The imidazolidone, pyrimidone and pyrrolidone compounds in the following examples are also known in the art as imidazolidinone, pyrimidinone and pyrrolidinone compounds, respectively.

EXAMPLE 1

This example illustrates the preparation of n-octylimidazolidone.

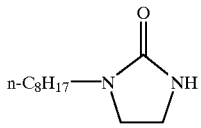

The starting diamine, N-n-octyl ethylene diamine was prepared from n-octyl chloride and ethylene diamine (Linsker and Evans, *J. Am. Chem. Soc.* 1945, 67, 1581–1582). This diamine (9.95 g, 0.058 mol) was reacted with urea (3.5 g, 0.058 mol) in a 50 mL 3-neck round bottom flask. The flask was equipped with a nitrogen inlet to flush the ammonia produced in the reaction out of the system and into a trap (dilute sulfuric acid). Ammonia evolution commenced at about 140° C. and heating was continued to 210° C. The temperature was held at this level for two hours to assure ring closure to the cyclic product. A small amount of material was sublimed from the reaction residue to give a white crystalline solid (mp 42.0–42.4° C.) which was used for all further measurements.

EXAMPLE 2

This example illustrates the preparation of n-octyl tetrahydropyrimidone (N-n-octylpropylene urea).

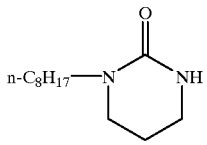

The starting diamine was prepared from n-octyl chloride and 1,3-propane diamine in a similar fashion to the ethylene diamine derivative of Example 1. It can also be synthesized by aminopropylation of n-octyl amine (Tarbell et al *J. Am. Chem. Soc.* 1946, 68, 1217–1219). Reaction with urea was performed as in Example 1 to give 91% yield of the product (mp 68–72° C., single peak by GC, no extraneous peaks by $^{13}C$ NMR).

EXAMPLE 3

This example illustrates the preparation of 1-methyl-3-octyl-2-imidazolidone (N-n-octyl-N'-methyl imidazolidone).

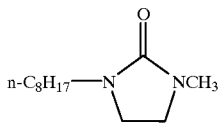

1-Methyl-2-imidazolidone (N-methyl imidazolidone) was prepared from diethyl carbonate and N-methyl ethylene diamine (Frick et al *Textile Res. J.* April 1959, 314–322). The reaction proceeded very slowly and the ethanol byproduct was distilled as it formed. Although not demonstrated in this work, this reaction is probably best performed in a pressure bomb or autoclave so that a higher temperature can be applied.

A three-necked 100 mL flask was fitted with an addition funnel, reflux condenser topped with an $N_2$ gas inlet, and a thermal well. Freshly ground KOH (3.6 g, 0.064 mol) and 20 mL THF (HPLC grade) were added. The apparatus was kept under $N_2$. Tetrabutyl ammonium hydrogen sulfate (0.34 g, phase transfer agent) and 1-methyl-2-imidazolidone (5.0 g, 0.050 mol) were then added. Upon gentle heating and stirring, a foamy mass formed that was difficult to stir. The mixture was agitated as well as possible and temperature was raised to 46° C. Octyl bromide (10.0 g, 0.052 mol) was then added through the addition funnel. After a few minutes, a sample was withdrawn and analyzed by GC. Several minutes after taking the GC sample, the mixture loosened up and the temperature rose quickly to 65° C. through self-heating. After holding a few minutes, the temperature then started to drop. A fine white solid was now present and the mixture was easily stirred. The temperature was raised to reflux temperature. The results of the first GC sample showed significant reaction had occurred at the time the sample was withdrawn, even though there was very little mixing at that time. After about 30 minutes of efficient stirring, GC analysis showed the reaction was almost complete. Heating was discontinued after an additional 20 minutes. The mixture was filtered and stripped on a rotary evaporator. The residue was distilled to give 3.5 g of a fraction boiling at 140–141° C. at 3 torr (43% yield) which was used in all further tests.

The other urea compounds of this invention were prepared similarly.

EXAMPLE 4

Dynamic surface tension data were obtained for aqueous solutions of n-octyl-pyrrolidone (See text after Table 2) using the maximum bubble pressure method at bubble rates from 0.1 bubbles/second (b/s) to 20 b/s. This compound is widely marketed to the coating and printing industries.

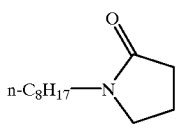

These data provide information about the performance of a surfactant at conditions from near-equilibrium (0.1 b/s) through extremely high surface creation rates (20 b/s). In practical terms, high bubble rates correspond to high printing speeds in lithographic printing, high spray or roller velocities in coating applications, and rapid application rates for agricultural products. The data are set forth in Table 1.

TABLE 1

Dynamic Surface Tension (dyne/cm) -- N-n-Octylpyrrolidone

| Concentration (wt %) | 0.1 b/s | 1 b/s | 6 b/s | 15 b/s | 20 b/s |
|---|---|---|---|---|---|
| 0.003 | 65.1 | 68.6 | 70.8 | 71.4 | 71.1 |
| 0.03  | 46.5 | 49.3 | 54.4 | 58.7 | 59.6 |
| 0.07  | 35.2 | 36.6 | 39.6 | 43.0 | 43.9 |
| 0.10  | 29.9 | 31.0 | 33.4 | 36.5 | 37.2 |
| 0.21  | 27.6 | 27.8 | 28.4 | 30.0 | 30.6 |

These data illustrate that n-octylpyrrolidone effectively reduced the surface tension of water under both static and dynamic conditions. A 0.1 wt % solution, for example, lowered the surface tension to below 30 dyne/cm at a surface creation rate corresponding to 1 b/s and was able to maintain a surface tension well below 40 dyne/cm even at the surface creation rate of 20 b/s.

EXAMPLE 5

Aqueous solutions of N-n-octylimidazolidone (Example 1) were prepared and their surface tensions were measured using the procedure described above. The data are set forth in Table 2.

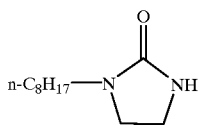

TABLE 2

Dynamic Surface Tension (dyne/cm) -- N-n-Octylimidazolidone

| Concentration (wt %) | 0.1 b/s | 1 b/s | 6 b/s | 15 b/s | 20 b/s |
|---|---|---|---|---|---|
| 0.010 | 52.8 | 58.2 | 64.2 | 68.6 | 68.8 |
| 0.025 | 43.2 | 47.1 | 53.2 | 57.1 | 57.7 |
| 0.050 | 35.4 | 38.2 | 43.1 | 47.2 | 47.6 |
| 0.100 | 28.0 | 29.7 | 33.1 | 37.5 | 37.9 |
| 0.205 | 26.7 | 26.9 | 28.2 | 32.4 | 33.8 |

The data show that N-n-octylimidazolidone has an ability to reduce the surface tension of aqueous systems which is superior to that of n-octylpyrrolidone, a compound which is widely marketed as a surfactant in the coating, ink, and adhesive industries. Like n-octylpyrrolidone, at a use level of 0.1 wt % in water, N-n-octylimidazolidone was able to provide a surface tension below 30 dyne/cm at 0.1 b/s, and maintain a surface tension well below 40 dyne/cm at 20 b/s. It has not previously been recognized that alkyl imidazolidones would have the ability to reduce the surface tension of an aqueous system. The ability to provide outstanding surface tension reduction in aqueous systems, and the fact that this material exhibits foam control (see Example 11) far superior to that of n-octylpyrrolidone would not be expected based upon the teachings of the prior art.

EXAMPLE 16

Aqueous solutions of N-n-octyltetrahydropyrimidone (n-OTHP; Example 2) were prepared and their surface tensions were measured using the procedure described above. The data are set forth in Table 3.

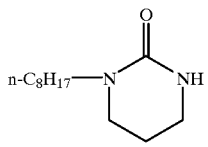

TABLE 3

Dynamic Surface Tension (dyne/cm) -- n-OTHP

| Concentration (wt %) | 0.1 b/s | 1 b/s | 6 b/s | 15 b/s | 20 b/s |
|---|---|---|---|---|---|
| 0.001 | 68.5 | 70.7 | 71.8 | 72.4 | 71.9 |
| 0.012 | 50.9 | 56.3 | 63.1 | 68.5 | 69.9 |
| 0.051 | 34.9 | 37.2 | 42.5 | 48.2 | 49.4 |
| 0.076 | 31.7 | 32.8 | 36.4 | 42.3 | 43.3 |
| 0.101 | 30.8 | 31.5 | 34.9 | 41.0 | 42.2 |

These data illustrate that alkyl propylene ureas can also be used in the practice of this invention since they effectively reduce the surface tension of aqueous systems. Indeed, at a 0.1 wt % use level in water, the ability of N-n-octyl tetrahydropyrimidone to reduce surface tension was outstanding. The ability of these types of materials to reduce the surface tension of aqueous systems, and produce substantially no foam (see Example 11) has not previously been recognized.

EXAMPLE 7

Aqueous solutions of 2-ethylhexyltetrahydropyrimidone (EHTHP) were prepared and their surface tensions were measured using the procedure described above. The data are set forth in Table 4.

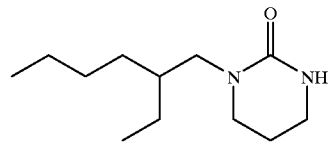

TABLE 4

Dynamic Surface Tension (dynes/cm) -- EHTHP

| Concentration (wt %) | 0.1 b/s | 1 b/s | 6 b/s | 15 b/s | 20 b/s |
|---|---|---|---|---|---|
| 0.001 | 65.7 | 68.7 | 70.4 | 70.8 | 70.6 |
| 0.010 | 57.0 | 61.2 | 66.2 | 69.4 | 69.9 |
| 0.050 | 42.4 | 44.4 | 47.8 | 52.0 | 53.1 |
| 0.100 | 35.9 | 37.6 | 39.9 | 42.8 | 43.9 |
| 0.150 | 32.3 | 33.5 | 35.4 | 37.7 | 38.8 |
| 0.248 | 29.5 | 29.8 | 31.0 | 32.7 | 32.6 |

These data illustrate cyclic ureas containing branched alkyl groups are also useful in the practice of this invention. The effect of branching is to increase the solubility of the material and decrease its efficiency. This is illustrated by comparing the data obtained for the 0.1 wt % solution with that of N-n-octyltetrahydropyrimidone in the previous example. At 0.1 wt %, 2-ethylhexyltetrahydropyrimidone provided a surface tension of 35.9 dyne/cm at 0.1 b/s compared to 30.8 dyne/cm for the compound of the previous example, indicating that more of the branched compound was required to obtain an equivalent reduction in surface tension. On the other hand, the branched compound has a higher solubility, and outstanding dynamic properties were observed at higher concentrations. In fact, at a use level of 0.25%, the surface tension can be maintained below 33 dyne/cm, even at the extremely high surface creation rate corresponding to 20 b/s. Again, this excellent performance is obtained without the introduction of foaming problems (see Example 11).

EXAMPLE 8

Aqueous solutions of isodecyloxypropyltetrahydropyrimidone (i-DOPTHP) were prepared and their surface tensions were measured using the procedure described above. The data are set forth in Table 5.

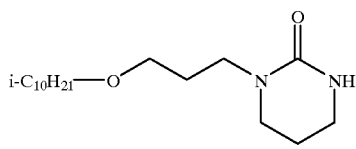

TABLE 5

Dynamic Surface Tension (dynes/cm) - i-DOPTHP

| Concentration (wt %) | 0.1 b/s | 1 b/s | 6 b/s | 15 b/s | 20 b/s |
| --- | --- | --- | --- | --- | --- |
| 0.001 | 69.4 | 71.7 | 72.3 | 73.0 | 72.5 |
| 0.005 | 55.7 | 69.9 | 72.0 | 72.9 | 72.9 |
| 0.010 | 33.7 | 54.1 | 67.4 | 71.6 | 71.8 |
| 0.050 | 27.0 | 30.4 | 51.7 | 59.0 | 61.5 |

These data illustrate that the novel cyclic ureas which contain oxygen in the alkyl substituent are also suitable for the practice of this invention. The compound of this example isodecyloxypropyltetrahydropyrimidone was extremely efficient, providing a surface tension of 27.0 dyne/cm at 0.1 b/s at the low concentration of 0.05 wt %. Thus this material would provide excellent performance at low use levels in applications in which the rate of surface creation is not very great.

EXAMPLE 9

Aqueous solutions of N-n-octyl-N'-methylimidazolidone (n-OMI; Example 3) were prepared and their surface tensions were measured using the procedure described above. The data are set forth in Table 6.

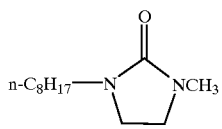

TABLE 6

Dynamic Surface Tension (dynes/cm) -- n-OMI

| Concentration (wt %) | 0.1 b/s | 1 b/s | 6 b/s | 15 b/s | 20 b/s |
| --- | --- | --- | --- | --- | --- |
| 0.011 | 50.2 | 55.8 | 62.0 | 68.3 | 68.1 |
| 0.020 | 44.2 | 49.2 | 55.5 | 59.7 | 60.1 |

TABLE 6-continued

Dynamic Surface Tension (dynes/cm) -- n-OMI

| Concentration (wt %) | 0.1 b/s | 1 b/s | 6 b/s | 15 b/s | 20 b/s |
| --- | --- | --- | --- | --- | --- |
| 0.100 | 29.1 | 30.1 | 34.6 | 38.7 | 39.0 |
| 0.500 | 26.2 | 29.0 | 29.7 | 30.8 | 31.3 |

These data illustrate that N-methylated imidazolidones are also suitable for the practice of this invention. Surfactant properties for this class of compounds have not been previously recognized.

EXAMPLE 10

Aqueous solutions of N-n-octyl-N'-methyltetrahydropyrimidone (n-OMTHP) were prepared and their surface tensions were measured using the procedure described above. The data are set forth in Table 7.

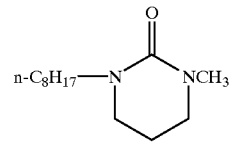

TABLE 7

Dynamic Surface Tension (dynes/cm) -- n-OMTHP

| Concentration (wt %) | 0.1 b/s | 1 b/s | 6 b/s | 15 b/s | 20 b/s |
| --- | --- | --- | --- | --- | --- |
| 0.0015 | 68.3 | 70.7 | 71.9 | 72.8 | 72.7 |
| 0.015 | 48.0 | 53.7 | 61.9 | 67.5 | 69.4 |
| 0.026 | 41.2 | 45.2 | 52.5 | 59.0 | 60.2 |
| 0.053 | 31.8 | 34.3 | 39.9 | 46.7 | 47.9 |
| 0.067 | 29.8 | 31.1 | 34.7 | 43.1 | 44.4 |
| 0.100 | 28.9 | 29.2 | 32.0 | 38.1 | 38.3 |

These data indicate that N-methylated tetrahydropyrimidones are also suitable for use in this invention.

EXAMPLE 11

The foaming properties of 0.1 wt % solutions of N-octylpyrrolidone and the cyclic urea surfactants according the invention were examined using a procedure based upon ASTM D 1173-53. In this test, a 0.1 wt % solution of the surfactant is added from an elevated foam pipette to a foam receiver containing the same solution. The foam height is measured at the completion of the addition ("Initial Foam Height") and the time required for the foam to dissipate at the air-liquid interface ("Time to 0 Foam") is recorded. This test provides a comparison between the foaming characteristics of various surfactant solutions. In general, in coatings, inks, and agricultural formulations, foam is undesirable because is complicates handling and can lead to coating and print defects, and to inefficient application of agricultural materials. On the other hand, robust foams can be of value in shampoos and other applications. The data is presented in Table 8.

TABLE 8

Foam Test Data

| Compound | Initial Foam Height (cm) | Time to 0 Foam or cm Foam after 5 min |
|---|---|---|
| Ex 4 (N-octyl pyrrolidone) | 4.0 | 1.0 cm |
| Ex 5 (N-octyl imidazolidinone, NH) | 2.5 | 20 s |
| Ex 6 (N-octyl tetrahydropyrimidinone, NH) | 1.5 | 10 s |
| Ex 7 (N-ethylhexyl tetrahydropyrimidinone, NH) | 1.5 | 3 s |
| Ex 8 (N-COCO tetrahydropyrimidinone, NH) | 2.0 | 1.0 cm |
| Ex 9 (N-methyl-N'-octyl imidazolidinone) | 4.0 | 2.0 cm |
| Ex 10 (N-methyl-N'-octyl tetrahydropyrimidinone) | 1.2 | 0.4 cm |

The data in Table 8 show that n-octylpyrrolidone is quite foamy, complicating its use in coating, ink, and agricultural formulations. In contrast, the compounds of the formula

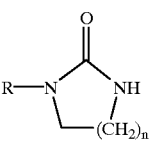

where R is a C8 alkyl group produced very little foam, and the foam which formed dissipated quickly. Thus these materials have desirable properties with respect to their use in coatings, inks and agricultural formulations.

In contrast, with the compounds of this invention in which R' is methyl, i.e., compounds of the formula

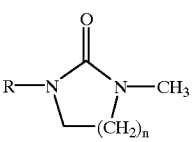

large amounts of long-lasting foam are formed. This property could be of value in shampoos and shaving creams, firefighting, enhanced oil recovery, mineral particle transport, or other applications where foam formation is important.

The ability of a surfactant in aqueous systems to reduce surface tension under both equilibrium and dynamic conditions is of great importance in the performance of water-based coatings, inks, adhesives, and agricultural formulations. Low equilibrium surface tension allows the development of excellent properties subsequent to application. Low dynamic surface tension results in enhanced wetting and spreading under the dynamic conditions of application, resulting in more efficient use of the formulations and fewer defects. In waterborne coatings, inks, adhesives, and agricultural formulations, the formation of foam is generally undesirable because it complicates handling and can cause defects or result in inefficient application. On the other hand, the formation of foam can be important in many other applications, and it is therefore desirable to be able to control the foaming characteristics of a surfactant so that its performance can be tailored for a specific application.

The N-(higher alkyl)-N'-methyl cyclic ureas of this invention display an outstanding ability to provide equilibrium and dynamic surface tension reduction in aqueous formulations while producing copious quantities of long-lasting foam. This combination of characteristics may be of value in ore flotation and mining, carpet shampoos, dishwashing detergent, shaving cream, or other applications where the formation of foam is of practical or aesthetic importance.

In contrast, the N-higher alkyl and alkoxyalkyl cyclic ureas display excellent ability to reduce equilibrium and dynamic surface tension while producing substantially no foam. These materials would therefore be expected to be useful in aqueous coating, ink, and agricultural formulations.

STATEMENT OF INDUSTRIAL APPLICATION

The invention provides compositions suitable for reducing the equilibrium and dynamic surface tension in water-based compositions.

We claim:

1. In a method for applying a water-based composition to a surface to partially or fully coat the surface, the composition containing an inorganic or organic compound and an effective amount of a surfactant for reducing the dynamic surface tension of the composition, the improvement which comprises employing as the surfactant a cyclic urea of the structure

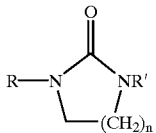

where R is a C6 to C12 alkyl group or R"O—(CH$_{2m}$-, R' is hydrogen or methyl, R" is a C4 to C12 alkyl group, m is 2–4 and n is 1 or 2, provided the organic compound is not an azole derivative fungicide.

2. The method of claim 1 in which an aqueous solution of the cyclic urea demonstrates a dynamic surface tension of less than 45 dynes/cm at a concentration of ≦5 wt % in water at 23° C. and 1 bubble/second according to the maximum-bubble-pressure method.

3. The method of claim 2 in which R is C7 to C10 alkyl.

4. The method of claim 2 in which R is R"O—(CH$_2$)$_m$- and R" is C6 to C10 alkyl.

5. The method of claim 4 in which m is 3.

6. The method of claim I in which the cyclic urea is N-n-octylimidazolidone; N-n-octyl tetrahydropyrimidone; 2-ethylhexyltetrahydropyrimidone; isodecyloxypropyltetrahydropyrimidone; N-n-octyl-N'-methylimidazolidone; or N-n-octyl-N'-methyltetrahydropyrimidone.

7. The method of claim 1 in which the cyclic urea is N-n-octylimidazolidone.

8. The method of claim 1 in which the cyclic urea is 2-ethylhexyltetrahydropyrimidone.

9. The method of claim 2 in which the measurement is made at 20 bubbles/second.

* * * * *